United States Patent
Borotto et al.

(10) Patent No.: US 10,595,975 B2
(45) Date of Patent: Mar. 24, 2020

(54) CAPACITIVE SENSOR ARRAY FOR DENTAL OCCLUSION MONITORING

(71) Applicant: ECOLE POLYTECHNIQUE FEDERALE DE LAUSANNE (EPFL), Lausanne (CH)

(72) Inventors: Marco Borotto, Pully (CH); Marco Letizia, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 171 days.

(21) Appl. No.: 15/310,110

(22) PCT Filed: May 22, 2015

(86) PCT No.: PCT/IB2015/053786
§ 371 (c)(1),
(2) Date: Nov. 10, 2016

(87) PCT Pub. No.: WO2015/181693
PCT Pub. Date: Dec. 3, 2015

(65) Prior Publication Data
US 2017/0265978 A1   Sep. 21, 2017

(30) Foreign Application Priority Data

May 26, 2014   (WO) .................. PCT/IB2014/061728

(51) Int. Cl.
*A61C 19/05* (2006.01)
*A61B 5/00* (2006.01)
(Continued)

(52) U.S. Cl.
CPC .............. *A61C 19/05* (2013.01); *A61B 5/228* (2013.01); *A61B 5/4542* (2013.01);
(Continued)

(58) Field of Classification Search
CPC ......... A61C 19/05; A61B 5/682; A61B 5/228; A61B 5/4547; A61B 5/4542;
(Continued)

(56) References Cited

U.S. PATENT DOCUMENTS 7,121,148 B2 * 10/2006 Starek .................... A61B 5/228
73/778
7,395,717 B2 * 7/2008 DeAngelis .............. G01L 1/146
73/724
(Continued)

FOREIGN PATENT DOCUMENTS

EP         3076402 A1   10/2016
JP    2008264024 A  *  11/2008
(Continued)

OTHER PUBLICATIONS

Machine translation of KR20120069846A.
(Continued)

*Primary Examiner* — Matthew M Nelson
(74) *Attorney, Agent, or Firm* — Andre Roland S.A.; Nikolaus Schibli

(57) ABSTRACT

The invention relates to devices, systems and methods exploiting capacitive means for monitoring and analysing teeth-related parameters in a subject, such as the dental occlusion profile and/or the load/force applied upon clenching. The device comprises a body such as a bite fork or bite splint, capacitive sensor(s) incorporated within a soft substrate reversibly deformable once bitten by a subject and a micro-controller unit. The teeth contact points and forces applied upon occlusion are measured via the sensors, delivered to and re-elaborated by the micro-controller unit and possibly sent and visualized in a graphical/numerical fashion on e.g. a display screen.

19 Claims, 12 Drawing Sheets

(51) Int. Cl.
*A61B 5/22* (2006.01)
*G01L 1/14* (2006.01)

(52) U.S. Cl.
CPC ............ *A61B 5/4547* (2013.01); *A61B 5/682* (2013.01); *G01L 1/146* (2013.01); *G01L 1/148* (2013.01); *A61B 2562/0247* (2013.01); *A61B 2562/046* (2013.01)

(58) Field of Classification Search
CPC ...... A61B 2562/046; A61B 2562/0247; G01L 1/148; G01L 1/146
USPC ..................................................... 433/68, 71
See application file for complete search history.

(56) References Cited

U.S. PATENT DOCUMENTS

| | | | |
|---|---|---|---|
| 9,561,002 B2 * | 2/2017 | Lau | ............................ A61J 9/00 |
| 2009/0151475 A1 * | 6/2009 | Masaki | ................... G01L 1/146 73/862.68 |
| 2010/0282000 A1 | 11/2010 | Gorjanc et al. | |

FOREIGN PATENT DOCUMENTS

| | | | |
|---|---|---|---|
| JP | 2008264024 A | * | 11/2008 |
| KR | 20120069846 A | | 6/2012 |

OTHER PUBLICATIONS

Patent Abstract of JP2008264024.
Diaz Lantada, A., González Bris, C., Lafont Morgado, P., & Sanz Maudes, J. (2012). Novel system for bite-force sensing and monitoring based on magnetic near field communication. Sensors, 12(9), 11544-11558.
International Search Report of PCT/IB2015/053786 dated Sep. 2, 2015.
Kim, J. H., McAuliffe, P., O'Connell, B., Diamond, D., & Lau, K. T. (2010). Development of wireless bruxism monitoring device based on pressure-sensitive polymer composite. Sensors and Actuators A: Physical, 163(2), 486-492.
Written Opinion of the International Search Authority dated Sep. 2, 2015.
European 1st Office Action dated Jul. 26, 2018 for counterpart 15 731 690.2.

* cited by examiner

CAPACITIVE SENSOR ARRAY FOR DENTAL OCCLUSION MONITORING

CROSS REFERENCE TO RELATED APPLICATIONS

The present application is a U.S. national stage application of PCT/IB2015/053786 filed on May 22, 2015 designating the United States, and claims foreign priority to International patent application PCT/IB2014/061728 filed on May 26, 2014, the contents of both documents being herewith incorporated by reference in their entirety.

TECHNICAL FIELD

The present invention is in the field of dentistry. It more precisely relates to the qualitative and quantitative monitoring of dental occlusion.

BACKGROUND ART

During the last years the engineering approach in dentistry is getting more importance. This is certainly due to the continuous improvements in complex surgical techniques. Occlusion issues have been highlighted in a significant number of scientific publications because of their consequences on health such as teeth damages and fractures, dental implants failure, headaches, back pain and postural problems. Monitoring of dental occlusion is also a fundamental tool which can be used after the insertion of dental implants. It may facilitate the restoration of a correct occlusion by balancing the jaw and preserving the implants themselves from extra loads.

Currently, the tooth contacts evaluation is achieved by the use of occlusal indicators, also known as articulating papers (FIG. 1a), important tools in identifying interferences and refining occlusal contacts during prosthodontic treatments. These marking strips are made of paper drenched by ink. Therefore, their main limitation is that they provide just a qualitative indication of location and number of tooth contacts without any information about the amount of jaw unbalance and the influence of each contact point.

Quantitative indicators employing electro-optic and resistive techniques, such as the TekScan® (see FIG. 1b) pressure measurement system, lack repeatability and sensitivity. Due to their stiffness and high thickness, this kind of device affects negatively the reliability of the results, providing an over-detection of contact points and generating a proprioreceptive response.

As of today, a complete, direct, objective and reliable characterization of the tooth contacts (dental occlusion) and/or the corresponding loads over the dental arch is still lacking.

SUMMARY OF INVENTION

The invention provides a solution to overcome the drawbacks of the prior art such as those described in the previous chapter. It concerns a device, system and methods in order to help dentists in monitoring patients' dental occlusion, measuring the load and/or the force applied over the dental arch upon clenching, or both, as described throughout the present disclosure and the appended claims.

During a dentistry examination, the accurate measurement of bite forces, occlusion and tooth contacts (see FIG. 2a), provides valuable information for diagnostic, treatment and prognostic purposes. The invention features at least one capacitive conductive sensor, preferably an array of sensors, incorporated in a flexible substrate, preferably a thin and soft pressure-sensible layer. The detection of tooth contacts can be performed by means of said soft and thin substrates which adapt to the teeth profile without influencing the jaw occlusion. Once the device bitten by the patient, the teeth contacts are detected, as well as, in some embodiments, the corresponding forces applied over the sensor(s) during clenching (see FIG. 3). The results are elaborated through an incorporated micro controller unit operatively connected to the sensor pad(s) via transmission conductive lines, and can be provided to an operator in the form of a visual and numerical representation about tooth contact location and/or relative forces.

According to the invention, the device may be used in different fields of dentistry, especially in odontology, prosthodontics and maxillofacial surgery, as bite-force measurements can provide additional information to e.g. help in evaluating the post-surgical evolution and to compare of alternative treatments. The device can also be used in the orthodontics field where the occlusal plane has to be frequently monitored during the recovery therapy or the dental pressure monitoring can provide the fundamental objective data useful to re-establish the correct occlusion after the therapy. Consequently, information about tooth contact points and relative loads represent new frontiers for dental treatments.

Accordingly, it is an object of the present invention to provide for a device for use in measuring dental occlusion of a subject through capacitive means, characterized in that it comprises:

a) a substrate reversibly deformable upon dental occlusion; and b) a sensor incorporated within said substrate comprising at least one capacitive pad and transmission conductive lines, said transmission conductive lines operatively connecting the capacitive pad to a micro controller unit.

In one embodiment, the device is characterized in that the sensor comprises an array of capacitive pads.

In one embodiment, the device is characterized in that the capacitive pad and/or the transmission conductive lines are made of a conductive metallic or polymeric material.

In one embodiment, the device is characterized in that the substrate comprises an elastomeric material.

In one embodiment, the device is characterized in that both the transmission conductive lines and the capacitive pad are deformable according to the deformation of the soft substrate upon dental occlusion.

In one embodiment, the device is characterized in that it is shaped as a bite fork or bite splint.

In one embodiment, the device is characterized in that it further comprises at least two shield layers embedded in the soft substrate located respectively above and under the sensor and connected to ground, wherein said shield layers are shaped as to reduce the electromagnetic interaction between a body part and the transmission conductive lines of the sensor due to a proximity effect.

Another aspect of the invention relates to a device for use in measuring the load and/or the force applied over all or part of the dental arch of a subject upon clenching, the dental occlusion, or both through capacitive means, characterized in that it comprises:

a) a substrate reversibly deformable upon clenching and/or dental occlusion;

b) a sensor incorporated within said substrate comprising at least one capacitive pad and transmission conductive lines, said transmission conductive lines operatively connecting the capacitive pad to a micro controller unit; and c) at least a two shielding pads incorporated within the substrate and located respectively above and under the sensor and in correspondence therewith, wherein said pads are operatively connected through transmission conductive lines to ground.

In one embodiment, the device is characterized in that the sensor and/or the shielding pads comprise an array of capacitive pads.

In one embodiment, the device is characterized in that the capacitive pad and/or the shielding pads and/or the transmission conductive lines are made of a conductive metallic material.

In one embodiment, the device is characterized in that the substrate comprises an elastomeric material.

In one embodiment, the device is characterized in that the transmission conductive lines, the shielding pads and the capacitive pad are deformable according to the deformation of the substrate upon clenching and/or dental occlusion.

In one embodiment, the device is characterized in that it is shaped as a bite fork.

In one embodiment, the device is characterized in that it further comprises at least two shield layers embedded in the soft substrate located respectively above and under the sensor and/or the shielding pads and connected to ground, wherein said shield layers are shaped as to reduce the electromagnetic interaction between a body part and the transmission conductive lines of the sensor due to a proximity effect.

A further object of the present invention relates to a system for use in measuring the load and/or the force applied over all or part of the dental arch of a subject upon clenching, the dental occlusion, or both through capacitive means, characterized in that it comprises:

a) a device as previously described; and b) an output system operatively connected to the micro controller unit of the device for analyzing and graphically/numerically displaying the load and/or the force applied over the dental arch upon clenching, the dental occlusion, or both.

A further object of the present invention relates to a method for measuring the load and/or the force applied over all or part of the dental arch of a subject upon clenching, the dental occlusion, or both through capacitive means by using the above described device and/or system.

DETAILED DESCRIPTION OF THE INVENTION

Figure 1A:
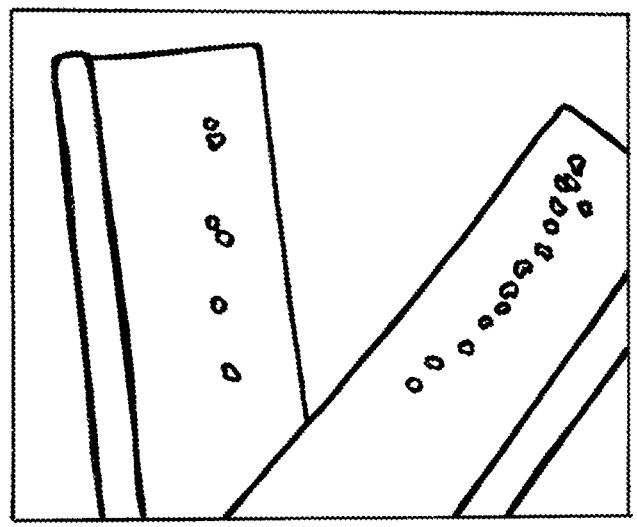
FIG. 1 shows prior art occlusion monitoring systems. (a) Articulating papers; (b) Semi-rigid resistive sensor by Tekscan®.
Figure 1B:
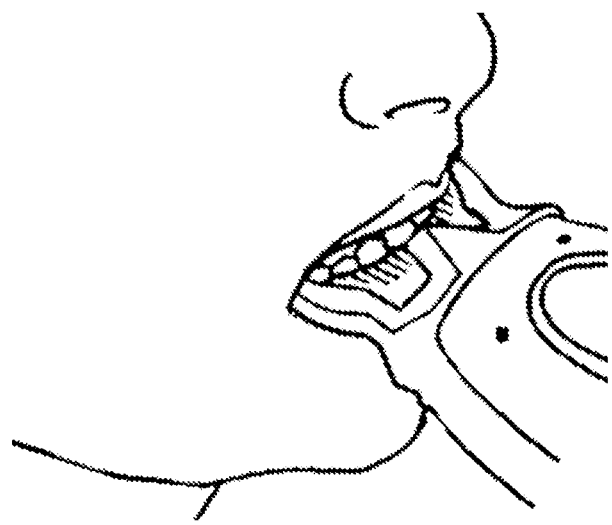
Figure 2A:
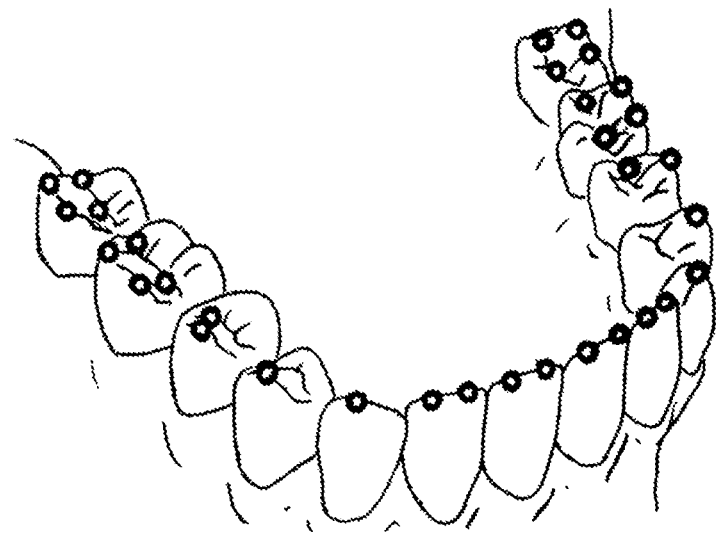
FIG. 2 shows occlusion monitoring. (a) Tooth contact points; (b) Typical shape of an intra-oral device for tooth contact monitoring; (c) Dental implants; (d) Dental relocation.
Figure 2B:
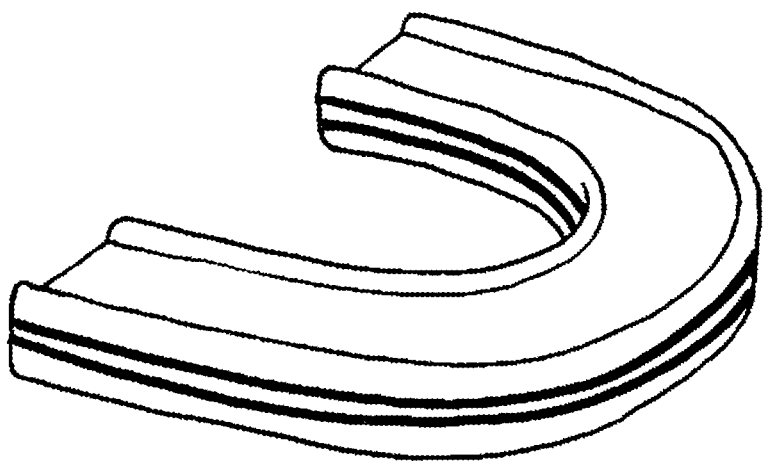
Figure 2C:
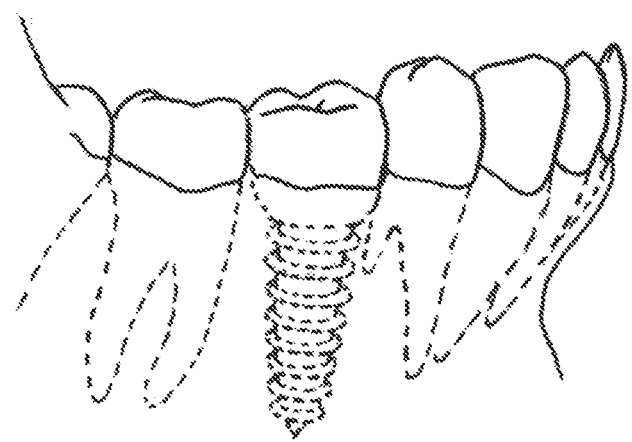
Figure 2D:
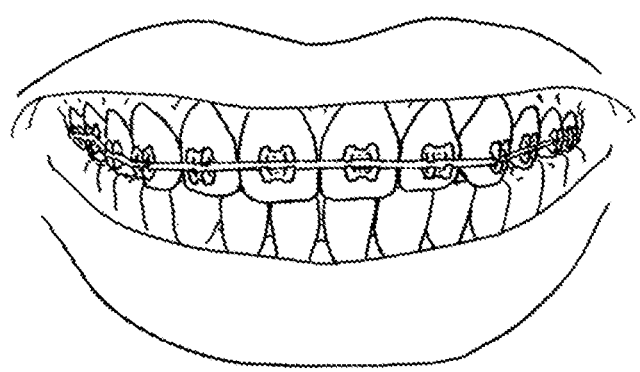
Figure 3A:
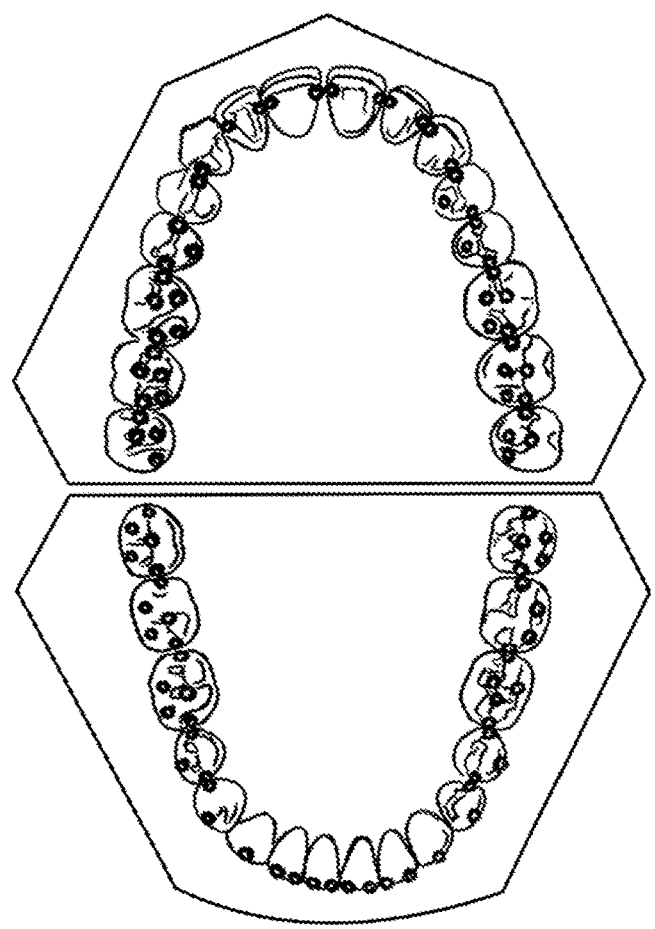
FIG. 3 shows teeth contact points. (a) Biting region; (b) Side-view of the teeth profile. The occlusal sensor has to follow the teeth profile for realistic force detection.
Figure 3B:
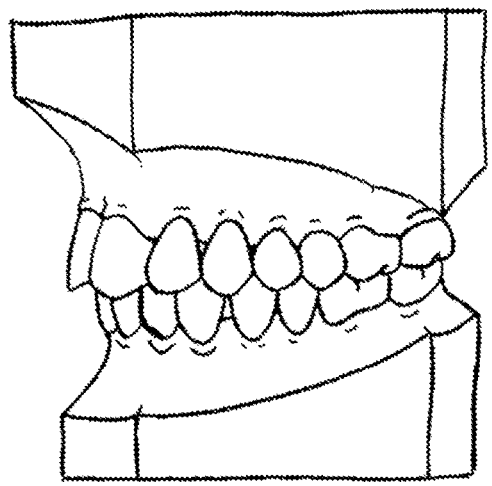

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a sensor" includes a plurality of such sensors and reference to "a transmission conductive line" includes reference to one or more conductive lines, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

The invention will be better understood with the help of the following definitions.

As used herein, "dental occlusion" refers to the contact between teeth. More specifically, it is the static or dynamic relationship between the maxillary (upper) and mandibular (lower) teeth when they approach each other, as occurs during e.g. chewing or at rest.

"Static occlusion" refers to contact between teeth when the jaw is closed and stationary, while "dynamic occlusion" (also termed as articulation) refers to occlusal contacts made when the jaw is moving. During chewing, there is no tooth contact between the teeth on the chewing side of the mouth.

Malocclusion, i.e. the misalignment of teeth and jaws, can cause a number of health and dental problems. It is the result of the body trying to optimize its function in a dysfunctional environment. It can be associated with a number of problems, including crooked teeth, gum problems, the temporomandibular joint (TMJ), and jaw muscles. Teeth, fillings, and crowns may wear, break, or loosen, and teeth may be tender or ache. Receding gums can be exacerbated by a faulty bite. If the jaw is mispositioned, jaw muscles may have to work harder, which can lead to fatigue and or muscle spasms. This in turn can lead to headaches or migraines, eye or sinus pain, and pain in the neck, shoulder, or even back. Malocclusion can be a contributing factor to sleep disordered breathing which may include snoring, upper airway resistance syndrome, and/or sleep apnea. Untreated damaging malocclusion can lead to occlusal trauma.

Some of the treatments for different occlusal problems include protecting the teeth with dental splints (orthotics), tooth adjustments, replacement of teeth, medication (usually temporary), a diet of softer foods, TENS to relax tensed muscles, and relaxation therapy for stress-related clenching. Removable dental appliances may be used to alter the development of the jaws. Fixed appliances such as braces may be used to move the teeth in the jaws. Jaw surgery is also used to correct malocclusion.

One of the key features of the device of the present invention is represented by the use, as a supportive framework for the electronics accountable for analysis and measurement of the dental occlusion and/or the clenching, of a substrate which reversibly deforms upon contact with teeth. This feature has the double action of optimizing the compliance of the device with the dental occlusion profile, thus hugely enhancing the measurements results, while being at the same time highly comfortable for a subject, such as a patient, using it. Therefore, generally speaking, suitable substrates in the frame of the invention are composed of, or comprises, an elastic material, i.e. a solid material having the tendency to return to its original shape after being compressed, stretched, expanded or otherwise deformed. Suitable elastic materials in this context are soft materials, a definition comprising any material that is either reversibly compressible, flexible, stretchable or any combination thereof. Preferred elastic materials are polymeric materials, elastomeric materials, thermoplastic elastomers (a class of copolymers or a physical mix of polymers, usually a plastic and a rubber, which consist of materials with both thermoplastic and elastomeric properties), foams, gels or hydrogels.

The term "foam", as used herein, refers to a substance that is formed by encompassing a plurality of polydisperse or monodisperse gas bubbles, referred to herein as "cells", within a mass of a liquid or a solid, constituting the films of walls separating the cells. In the context of solid foams, according to some embodiments of the invention, the regions occupied by a tangible condensed mass are regarded as the "solid" fraction of the foam, while all other regions not occupied by this fraction are regarded as the "gas" fraction of the foam. According to some embodiments of the present invention, the foam is a combination of a polymeric porous solid matrix and gas-filled cells, typically filled with ambient air. The phrase "porous solid matrix", as used herein, refers to the non-gaseous part of the foam, which contributes substantially to the mass of the foam but substantially less to its volume. Typical foams suitable in the frame of the present disclosure are those like PDMS foam HT-800, Rogers Corporation®.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

A non-exhaustive and non-limiting list of suitable elastic materials according to the present invention comprises polymeric materials such as silicone (for example polydimethylsiloxane PDMS), nitrile rubber, polyimide, latex, polyurethane, polyisoprene (synthetic rubber), any kind of elastomers, the Tango family of rubber-like materials (for example TangoPlus or FullCure930), polyurethane foam (foam rubber), XPS foam, polystyrene foam, phenolic foam, styrenic block copolymers, polyolefin blends, elastomeric alloys, thermoplastic polyurethanes (TPU), thermoplastic copolyester, thermoplastic polyamides and the like.

An elastic material is particularly suitable for the manufacturing of the device of the invention, since it could permit an almost perfect compliance with the teeth profile upon dental occlusion or clenching, and provides a high reliability in terms of measures obtained upon its use on a patient.

As used herein, the wording "operatively connected", "operatively connectable" or even "operatively connecting", reflects a functional relationship between two or more components of a device or a system, that is, such a wording means that the claimed components must be connected in a way to perform a designated function. The "designated function" can change depending on the different components involved in the connection; for instance, the designated function of a micro controller unit operatively connected to a display system is the (re-)elaboration and dispatch of the data relative to dental occlusion and/or clenching coming from the sensor to said display system. In the same way, the designated function of transmission conductive lines operatively connecting a capacitive pad to a micro controller unit is the transmission of an electrical signal from one component (the sensor pad) to another (the micro controller). A person skilled in the art would easily understand and figure out what are the designated functions of each and every component of the device or the system of the invention, as well as their correlations, on the basis of the present disclosure.

The elastic support substrate comprises a sensor which is incorporated, preferably embedded, within it. A "sensor" as used herein is a device that detects (and possibly responds to) signals, stimuli or changes in quantitative and/or qualitative features of a given system, or the environment in general, and provides a corresponding output. The output is generally a signal that can be converted to human-readable display at the sensor location or transmitted electronically over a network for reading or further processing. The specific input in the precise context of the invention is the pressure applied on said sensor. Accordingly, a sensor of the invention comprises a means for detecting and transmitting an information related to a pressure applied thereon upon dental occlusion, clenching or both. Said information is then delivered towards a micro-controller unit that elaborates and possibly stores and/or transmit the obtained information.

The sensor of the invention generally comprises two main components, namely a capacitive pad appointed to the detection of the pressure signal(s) upon dental occlusion/clenching, and a transmission conductive line that electrically transmits the detected signal to a micro-controller unit. For "capacitive pad" is herein meant any kind of detection element which works by exploiting a capacitance effect. Capacitance is the ability of any object that can be electrically charged to store an electrical charge. A common form of energy storage device is a parallel-plate capacitor. In a parallel plate capacitor, capacitance is directly proportional to the surface area of the conductor plates and inversely proportional to the separation distance between the plates. Accordingly, in its simplest embodiment, the capacitive pad included in the sensor according to the present invention is a capacitor. A "capacitor", or "condenser", is a passive two-terminal electrical component used to store energy electrostatically in an electric field. The forms of practical capacitors vary widely, but all contain at least two electrical conductors (e.g. plates) separated by a non-conductive region called dielectric or insulator. The conductors can be thin films, foils or sintered beads of metal or conductive electrolyte, etc. The non-conducting dielectric acts to increase the capacitor's charge capacity. Typical dielectrics can be glass, ceramic, plastic film, air, vacuum, paper, mica, oxide layer etc. Capacitors are widely used as parts of electrical circuits in many common electrical devices. Unlike a resistor, an ideal capacitor does not dissipate energy. Instead, a capacitor stores energy in the form of an electrostatic field between its plates.

When there is a potential difference across the conductors (e.g., when a capacitor is attached across a battery), an electric field develops across the dielectric, causing positive charge +Q to collect on one plate and negative charge −Q to collect on the other plate. If a battery has been attached to a capacitor for a sufficient amount of time, no current can flow through the capacitor. However, if a time-varying voltage is applied across the leads of the capacitor, a displacement current can flow. The capacitance is greater when there is a narrower separation between conductors and when the conductors have a larger surface area. In practice, the dielectric between the plates passes a small amount of leakage current. Actually, according to at least some embodiment of the invention, the two electrical conductors of the capacitor of the sensor are represented on one side by the capacitive pad, and on the other hand by a body part, most preferably a tooth, approaching said capacitive pad.

In another embodiment, a conductive pad is created by the inter-crossing of two conductive elements. For example, two linear conductive elements such as stripes, wires or bands are placed in the device substrate, such as e.g. embedded therein, on the same or different parallel planes and with a 90° arrangement between them, in parallel at the same time also with the dental occlusion plane. The conductive elements basically work as sensors, arranged in some embodiments as a layer of rows and a layer of columns; the intersections of each row and column represent unique touch coordinate pairs.

The conductive pads of the sensor are shaped, sized and/or placed in the device usually accordingly to the needs and applications foreseen for the device. For example, where the device shall measure e.g. a maximum force/load, the pad(s) can be placed in a portion of the device in correspondence with the molar teeth. In the same way, for such an application, the dimensions (surface area, thickness etc.) and materials used would be chosen in order to maximise and optimize the sensor's response to a strong clenching.

A "transmission conductive line" is any element that allows the flow of electrical current in one or more directions, i.e. it is an electrical conductor (such as a wire) or interconnect able to transport an electrical signal from one site to another and vice versa. In particular, in the frame of the invention, a transmission conductive line operatively connects a capacitive pad to a micro-controller unit so that an electrical current output, created by the alteration in capacitance sensed by the pad approached by teeth, can be transmitted to the microchip for data re-elaboration and analysis.

In some embodiment, the sensor comprises a plurality (array) of capacitive pads and/or a plurality of transmission conductive line operatively connecting the formers to one or more micro-controller units. This design is particularly useful in order to enhance the sensitivity or the resolution of the sensor. For example, in one embodiment of the invention, an array of pads are embedded within the support substrate and disposed in a planar fashion, in parallel to the dental occlusion plane. Once approached by teeth upon dental occlusion, the sensor's capacity changes due to the proximity of the tooth's cusps to the pad, thus altering the sensor's electric field at rest. The pads are able to reveal the contact points and can therefore provide a precise, qualitative spatial measure of the dental occlusion, thus permitting to an operator such as a clinician to estimate a possible malocclusion and tailor a therapy accordingly. As it will be apparent, the higher the number of pads will be in this kind of pads' array, the higher the spatial resolution of the sensor. In practice, by exploiting such a design, the device of the invention functions as an "electronic articulating paper".

The elements composing the sensor shall comprise, for their functioning, an electrically conductive material. Any suitable material able to conduct and electrical current can be used for the manufacturing of the sensor, including but not limiting to metallic conducting materials such as copper, silver, gold, aluminium and the like as well as alloys or oxides thereof, liquid metals such as gallium, mercury etc. as well as alloys or oxides thereof, conductive composite materials such as polymer-metals pastes, polymeric materials and so forth. In some embodiments, some or all of the elements composing the sensor can be formed on the substrate material or on a different deformable support material embedded within the substrate material by electron beam evaporation, thermal evaporation, sputter deposition, chemical vapour deposition (CVD), electro-plating, molecular beam epitaxy (MBE) or any other suitable means.

In some embodiments of the invention, some or all of the elements composing the sensor are deformable according to the deformation applicable to the substrate of the device. Electrically conducting structures such as films or interconnects can be stretched far when they are made on easily deformable substrates. When tightly bonded to the substrate, the electrically conducting structures remain electrically conducting to high values of extension and can be used as stretchable electrical interconnections. When the substrate is made substantially of a deformable material such as an elastomer, electrical conductance is retained over multiple cycles of stretching and relaxation, and such films on elastomeric substrates can be used as e.g. elastic, space-saving electrical interconnects. This kind of stretchable interconnects are usually obtained by simply covering e.g. flexible and/or reversibly stretchable substrates with one or more films of conductive materials by any of the above-mentioned means. In some embodiments, an electrically conductive material having adhesive properties to the substrate material is used singly or in combination with one or more additional layers, for example, a first conductive film of e.g. chromium can be applied to the substrate as an adhesive layer and a second conductive film of e.g. gold can be applied to the chromium layer.

In some embodiments of the invention, at least two additional shield layers can be added to the device. A "shield layer" as used herein is an element such as a film substantially composed of a conductive material, preferably a metallic conductive material, which is used to optimize the resolution of the sensor's signal. Generally speaking, the at least two shield layers are placed in the device, preferably embedded therein, in order to reduce the electromagnetic interaction between a body part and the transmission conductive lines of the sensor due to a proximity effect. This permits to reduce the cross-talk between the conductive pads and to avoid false-positive contact signals due to the change in conductance at the transmission lines level, especially when the device envisages an array of conductive pads. In fact, in view of several different parameters that can affect the analysis of dental occlusion (form and/or size of the teeth, occlusion plane, number and/or form of the conductive pads just to cite some), the output of the dental occlusion/clenching analysis can be biased as a result of an alteration of the electrical field at the transmission conductive lines level, which is nonetheless part of the device's sensor(s). The aim of the additional shield layers is to reduce as much as possible this drawback by "shielding" the conductive lines so to have a cleaner signal and a more reliable measure of dental occlusion.

Figure 4:
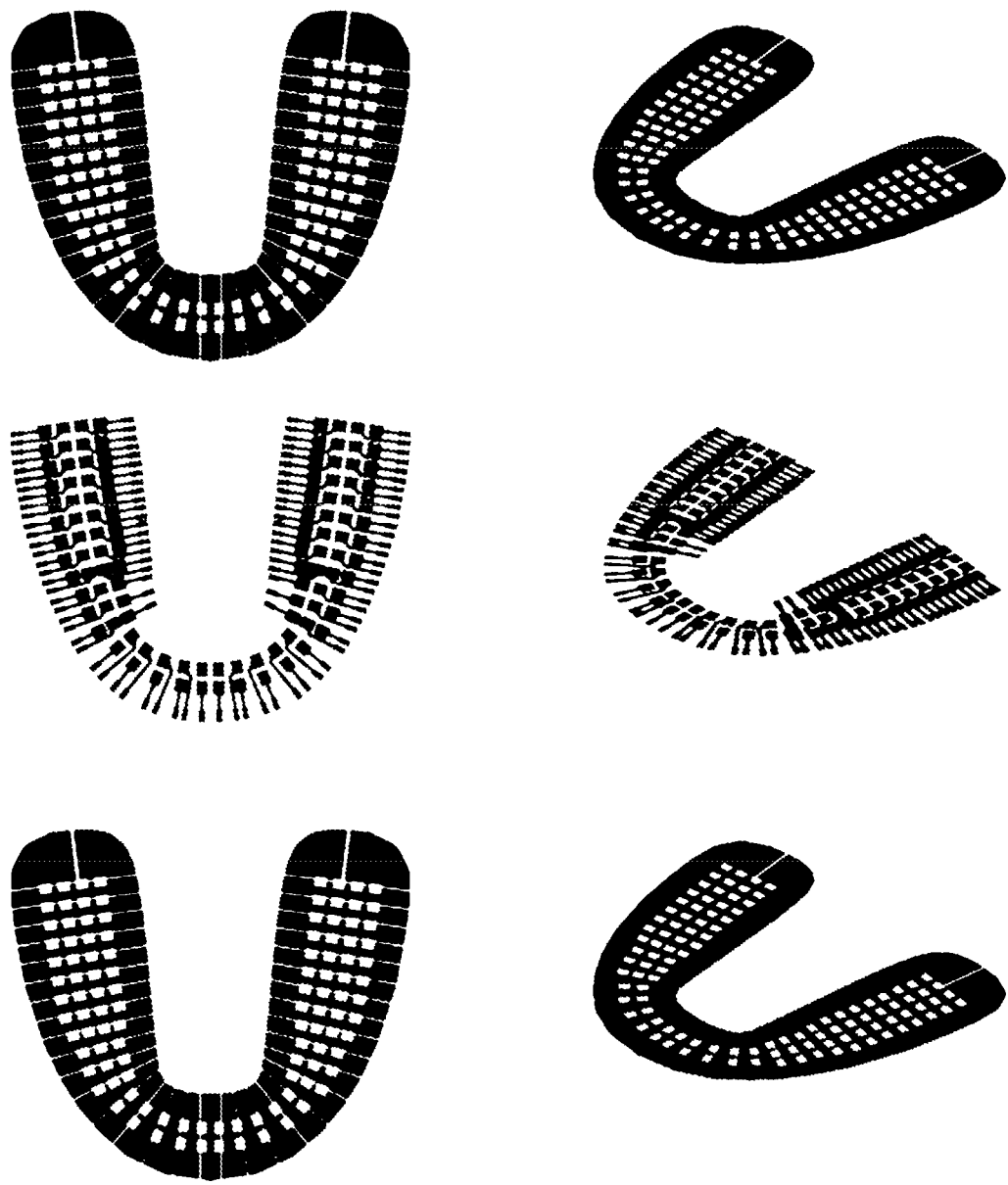
FIG. 4 depicts an exploded view of a sensor array (middle image) sandwiched between two shield layers (upper and lower images).

To do so, the shield layers must be designed and put into the device in such a way as to "protect" only the transmission conductive lines; in particular, one shield layer is place above the sensor while another one is placed under the sensor. The layers are shaped in a mirror-like fashion compared to the sensor, as depicted in an exemplary embodiment in FIG. 4. In such a way, only the conductive pads remain the active elements of the sensor(s) for what concern the detection of a change in the electric field. In order to perform their shielding action, the shield layers are connected to ground so that no change in the electric field can be detected at the transmission lines level upon dental occlusion. Ideally, the shield layers are deformable according to the deformation of the substrate material of the device, and can be manufactured according to the same procedures and materials already described for the sensor.

Capacitive sensing suffers from interferences from external noise sources (e.g., in the form of electromagnetic waves) or from external objects in the proximity of the sensor. In many applications, where the capacitive sensing is mainly used to detect the presence of a body, the capacitive elements (pads) have to be non-shielded. In case of application that require quantitative sensing of force/load/pressure, a shielding solution avoids external disturbs affecting the measurements. Force/Load/Pressure sensors, for instance, need to sense only once they are pressed even if the external object gets close to the sensor. Furthermore, the human body, being essentially made of lossy dielectric materials, shows a proper capacitance (in the order of 100-200 pF) and a proper resistance (few MOmh) that, in case of proximity of a non-shielded capacitive sensor, changes the electrical response of the sensor that eventually produces artifacts in the sensing. If a capacitive sensor is used to quantitatively detect a pressure/force applied, a proper shield solution is required.

Accordingly, a further object of the invention relates to a device for use in measuring the load and/or the force applied over all or part of the dental arch upon clenching, the dental occlusion, or both through capacitive means. Such a device exploits and shares most of the principles of the device previously described. However, this device comprises in addition at least a two shielding pads incorporated within the substrate and located respectively above and under the sensor and in correspondence therewith, wherein said pads are operatively connected through transmission conductive lines to ground (see for example FIG. 5). Such a setting provides a sensing structure that allows for precise quantitative measurement of the force/load applied on the sensor upon dental occlusion/clenching. A "shielding pad" as used herein is an element such as a film substantially composed of a conductive material, preferably a metallic conductive material, connected to ground, which is used in the device in order to implement the measure of the load and/or the force applied over all or part of the dental arch upon clenching, the dental occlusion, or both once coupled with a sensor as the one previously described. Generally speaking, the at least two shielding pads are placed in the device, preferably embedded therein, in order to reduce the electromagnetic interaction between a body part and the conductive pads of the sensor due to a proximity effect. In particular, one shielding pad is place above the sensor while another one is placed under the sensor. Ideally, the shielding pads shift along the pressure axis according to the deformation of the substrate material of the device that incorporates them, and can be manufactured according to the same procedures and materials already described for the sensor. In order to perform their shielding action, the shielding pads are connected to ground so that no change in the electric field can be detected at conductive pads level upon dental occlusion/clenching. The shielding pads can have any suitable shape, as long as they are placed in correspondence of the entire surface of (a) conductive pad(s) in order to perform their action.

Figure 6:
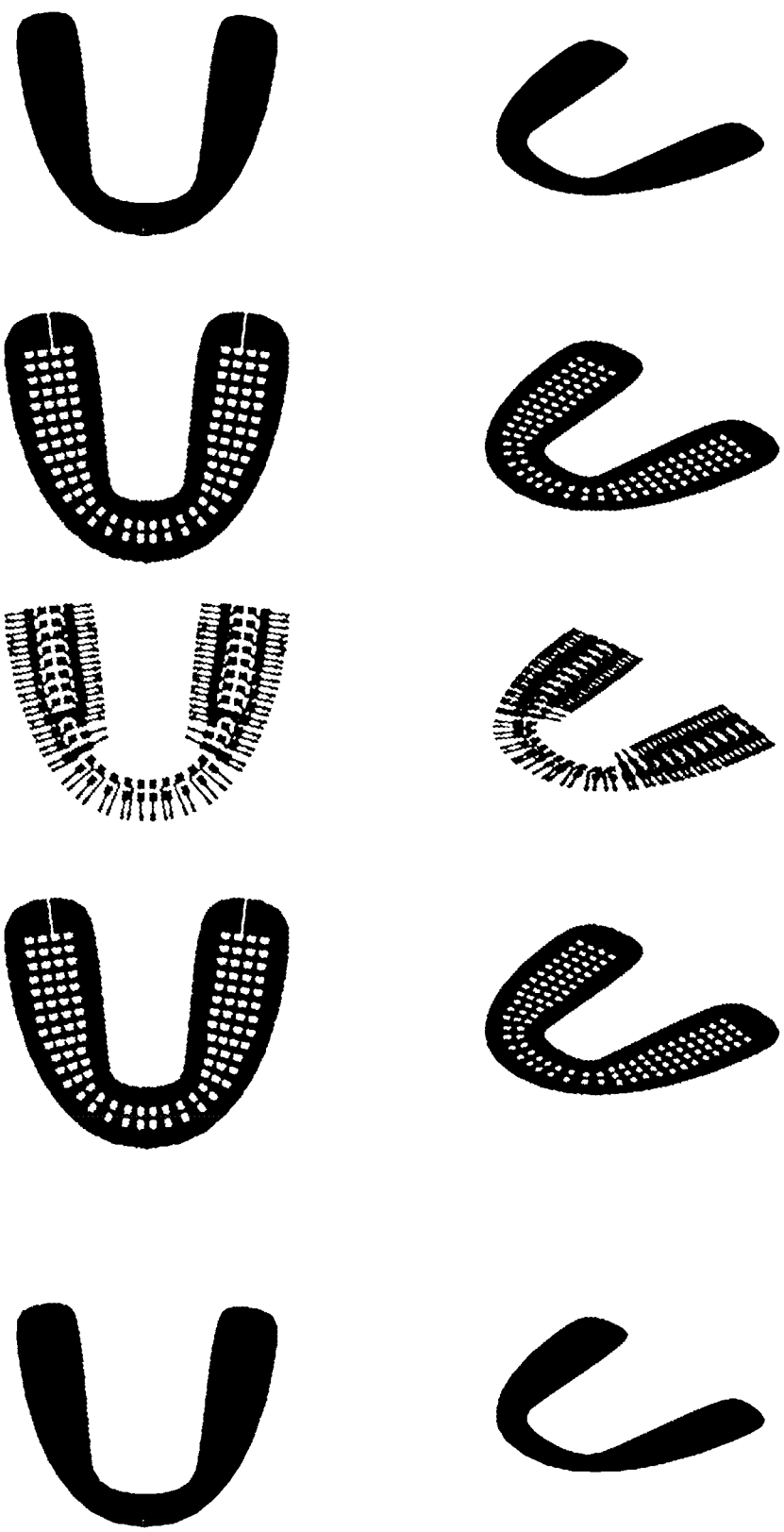
FIG. 6 depicts an exploded view of a sensor array (middle image) sandwiched between two shield layers as the one depicted in FIG. 4, further comprising two shielding pads (top and bottom images).

Advantageously, at least two shield layers as described above can be combined also into a device comprising the shielding pads. In such a design, as the exemplary one depicted in FIG. 6, the above illustrated shielding effect of the shield layers can be exploited even in a device for use in measuring the load and/or the force upon dental occlusion and/or clenching in a subject. Preferably, in order to maximize the signal-to-noise ratio and avoid interferences, the shield layers are included (e.g. embedded) in the device closer to the sensor, while the shielding pads are placed one above and one under said shield layers. In order to have a more reliable measure, all the element of the device, namely the sensor(s) (and in particular the conductive pads), the shield layers and the shielding pads, are most preferably parallel between them, and generally with the dental occlusion plane.

A "micro-controller unit", or microchip, is a small computer, generally designed for embedded applications, on a single integrated circuit containing a processor core, memory, and programmable input/output peripherals. A micro-controller can be considered a self-contained system, some of which being very sophisticated, while others have minimal requirements for memory and program length, with no operating system, and low software complexity. Typical input and output devices include switches, relays, solenoids, LEDs, small or custom LCD displays, radio frequency devices, and sensors for data such as temperature, humidity, light level etc.

In the frame of the present invention, the micro-controller unit is the element of the whole device appointed to the processing of the received information, and can even further comprise a data storage device to hold information. Common used data storage devices include memory cards, disk drives, ROM cartridges, volatile and non-volatile RAMs, optical discs, hard disk drives, flash memories and the like. Preferably, the micro-controller unit further comprises a means for transmitting the detected and/or stored data concerning the above-mentioned parameters to a computer, and more preferably through a wireless connection. "Wireless" refers herein to the transfer of information signals between two or more devices that are not connected by an electrical conductor, that is, without using wires. Some common means of wirelessly transferring signals includes, without limitations, WiFi, bluetooth, magnetic, radio, telemetric, infrared, optical, ultrasonic connection and the like.

A micro-controller unit is, according to the present disclosure, operatively connected to the sensor's transmission line(s) and can in some embodiments be embedded in, or otherwise physically attached to, a portion of the device so to not disturb the sensor's measurements, in order to have an all-in-one tool that can be possibly operatively connected to a display system.

The entire device can have any suitable shape, as long as such a shape allows the measurement of the dental occlusion, the clenching or even both. For example, the device can be shaped, depending on the applications and/or the needs, as a strip, a band, a cylinder, a patch or preferably as a bite fork that can be comfortably inserted into a subject's mouth and cover even the entire dental arch.

A further object of the invention relates to a system for use in measuring the load and/or the force applied over all or part of the dental arch of a subject upon clenching, the dental occlusion, or both through capacitive means, characterized in that it comprises a device as previously described and an output system operatively connected to the micro controller unit of the device for analyzing and graphically/numerically displaying the load and/or the force applied over the dental arch upon clenching, dental occlusion, or both. The system is generally characterized by the device of the invention coupled with a computer-based system that provides a graphical/numerical visual output, via for instance a monitor showing the teeth contact points of a subject's upon dental occlusion, or the force/load applied by the subject upon clenching. Such a system is particularly useful for methods for measuring the load and/or the force applied over all or part of the dental arch of a subject upon clenching, the dental occlusion, or both, that form also part of the present disclosure. Such methods can be used in several desperate applications in the dentistry field, as for instance those listed below:

Jaw Force and Electromyograph (EMG) Correlation

Instead of looking for tooth contacts to determine the jaw unbalance after dental implants, teeth reconstruction, dental relocation or all cases in which the correct occlusion has to be re-established, an electronic device called electromyograph has been used so far.

It is composed by many electrodes applied in specific facial regions characterized by the presence of muscles involved in the mastication process. This electronic device is able to detect the electrical signal provided by the muscles during the clenching. Looking at the different signals from the left and right side, it is possible to achieve an occlusal analysis to determine the balance or unbalance of the jaw.

The results, although giving reliable and quantitative values, provide information just in terms of electrical signal. With this approach, the information about the unbalance in terms of loads is missing. This parameter would be meaningful to evaluate the entity of a certain unbalance and also discriminate patients with same percentage of unbalance but with different loads. For instance, two different patients with the same 20% of unbalance between left and right side but with different maximum loads during the clench should be differently treated.

The system of the invention can improve the application of electromyography providing the (quantitative) load information that now is missing. Two additional rigid layers might be added in contact to the external armature to keep the sensor stiff and to obtain the total vertical load provided by the muscles.

Electromyograph Technical Layout Description

Figure 7A:
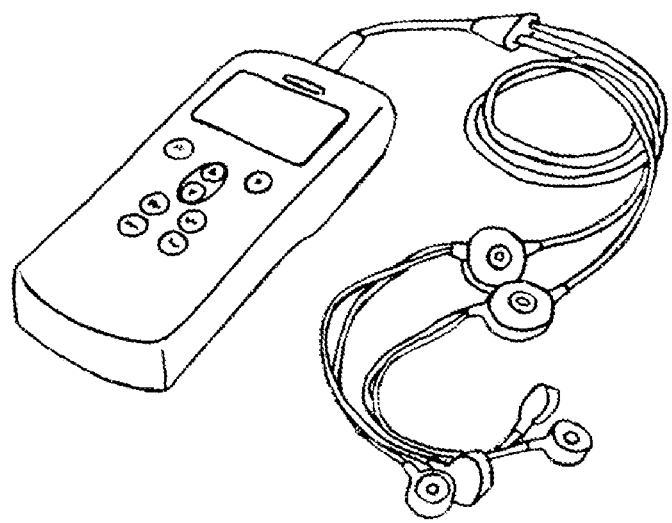
FIG. 7 shows and electromyograph (EMG) system. (a) Electromyograph device; (b) Operation and data.
Figure 7B:
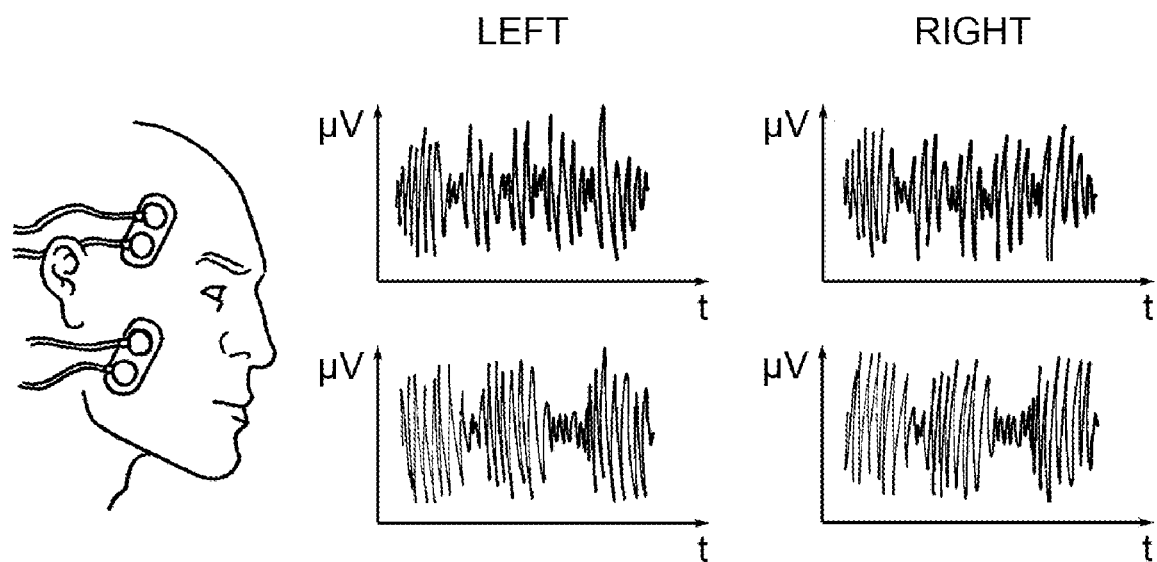

A common electromyograph is shown in FIG. 7a while FIG. 7b represents a possible use of this kind of device to determine the temporal and masseter muscles activity. As shown in FIG. 7b, by monitoring the intensity of the signals from different electrodes, the unbalance between the muscles on left and right side can be detected. The clinician can consequentially act in order to solve this problem. The identification of the main values for determining the balance/unbalance is submitted to precise and known clinical protocol.

Electromyograph Correlation with Pressure Sensor

Figure 8:
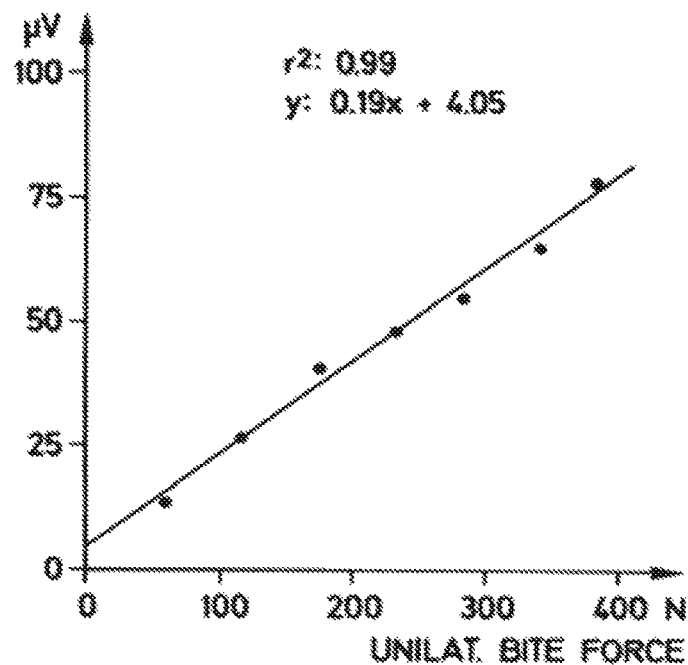
FIG. 8 shows a linear correlation between jaw force and EMG activity (taken from A. D. Lantada et al, *Sensors* 2012, 12, 11544-11558, August 2014.

The purpose is to obtain the load applied over the dental arch and estimate the unbalance in terms of force starting from an electromyographic signal. It is known that a linear dependence exists between the force exerted and the EMG signal (as shown in FIG. 8). The parameters of such linear correlation are extracted by measuring simultaneously the EMG signal and the load recorded, while a low level of clench is exerted by the patient. The load and EMG signals in correspondence to a heavy clench cannot be safely recorded because it is not possible for the patient to clench heavily when a rigid sensor is hold between the teeth. Afterwards the load sensor can be removed. At this point, the linear correlation existing between force and EMG signal is completely characterized. Thus, the maximum force exerted as well as the force as variation of time can be extrapolated starting from the value of the electrical signal measured by the EMG while the patient is freely clenching.

Bruxism Monitoring

Bruxism is a pathology consisting of grinding or tight clenching of the jaw, which leads to several problems such as teeth damages, headaches, orofacial pain and important disorders of the temporomandibular joint.

Figure 9:
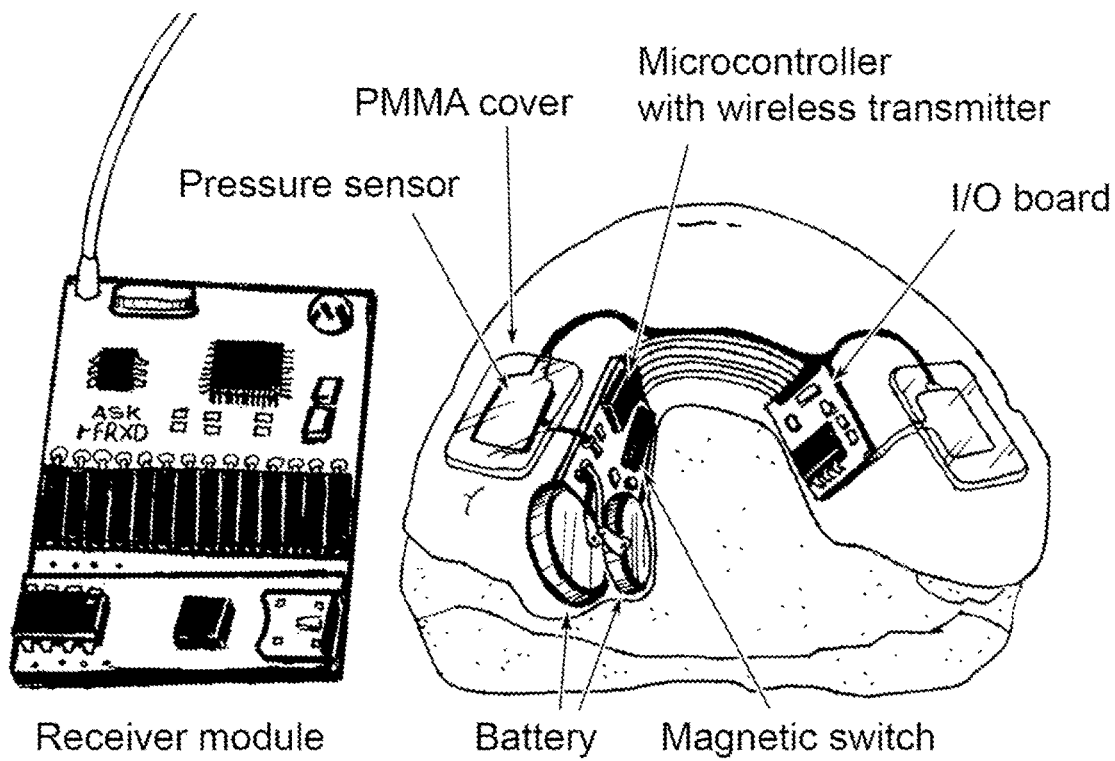
FIG. 9 shows resistive sensors in carbon-black are embedded in a bite splint to monitor bruxism (taken from J. H. Kim et al, "*Development of wireless bruxism monitoring device based on pressure-sensitive polymer*").
Figure 10:
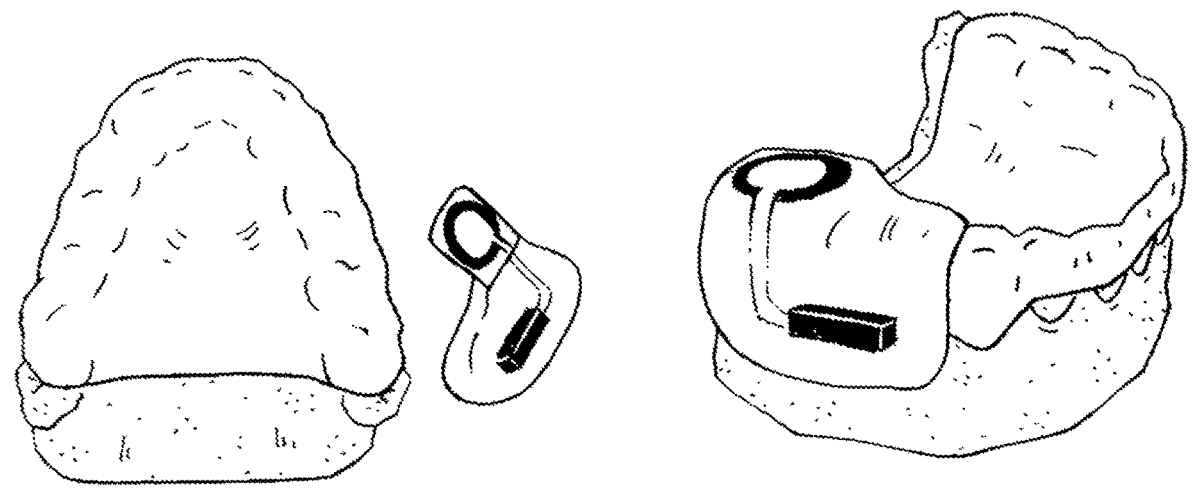
FIG. 10 shows piezo-electric sensors from TekScan embedded in a bite splint to monitor bruxism (taken from A. D. Lantada et al, *Sensors* 2012, 12, 11544-11558, August 2014.

Several devices have been developed in the past two decades for monitoring the jaw activity during night time, allowing intraoral bite-force sensing using different mechanical and electronic sensing principles, mainly based on strain-gauges, carbon-black sensors (FIG. 9) or piezoelectric sensors (FIG. 10). In any of these cases, the force sensors are based on the resistive approach yielding in rigid, bulky and uncomfortable devices.

The use of the system of the present invention, based on a device comprising a soft and stretchable substrate, provides in at least some embodiments a very compact and bio-compatible bite splint assembly. This solution is simple to be manufactured, more comfortable for a patient and more reliable in terms of measurement outcomes with respect to the existing solutions, mainly thanks to natural adaptation of the device's external soft surface with the patient's dental occlusion profile.

Contact Points Evaluation and 3D Virtual Dental Model

Figure 11A:
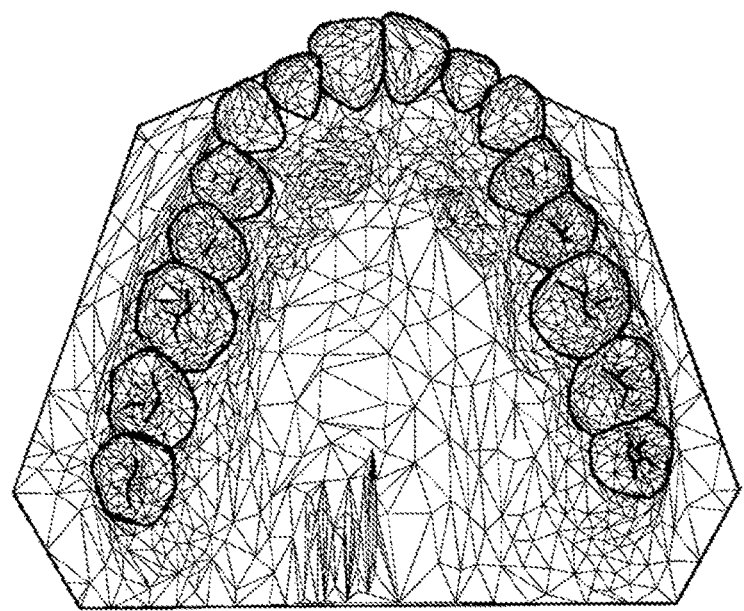
FIG. 11 shows virtual dental models. (a) 3D digital reconstruction of the dental arch; (b) superimposition of the contact point analysis.

Three dimensional virtual dental models provide a 3D digital reconstruction of the dental arches (FIG. 11a). This process is currently used in dental clinics to reconstruct, with high accuracy, the dental model of the patient. Successively, the digital model is used in dental CAD-CAM applications, reverse engineering or quality control for prosthesis and dental devices.

Figure 11B:
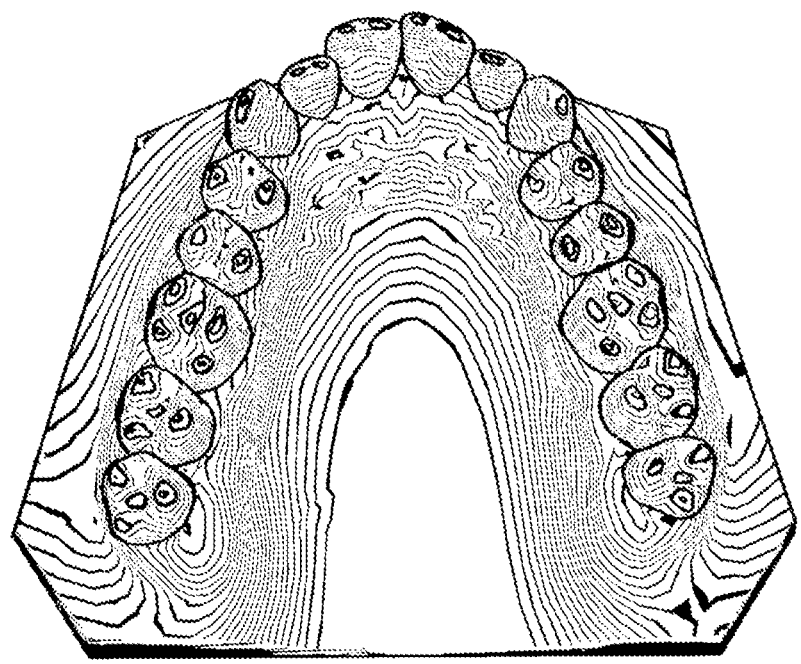

The possibility of superimposing the force distribution and the tooth contact points along the dental arch to the virtual models (as shown in FIG. 11b) opens up further visual perspectives when considering every-day clinical treatments in dentistry. Once the contact/force measurements have been performed, the data obtained by the disclosed sensor can be integrated in existing dental CAD software.

To describe and illustrate more clearly the present invention, the following exemplary preferred embodiments are provided in more details, which are however not intended to be limiting of the invention, and modifications will be apparent to those skilled in the art. In particular, the dimensions, materials as well other parameters can be varied, for example to adapt the device or the system of the invention to various applications and/or to manufacturing constraints, material limitations, etc. The general principles defined in the following description would be applied to other embodiments, alternatives, modifications, equivalents, and applications without departing from the spirit and scope of the present invention.

Figure 12:
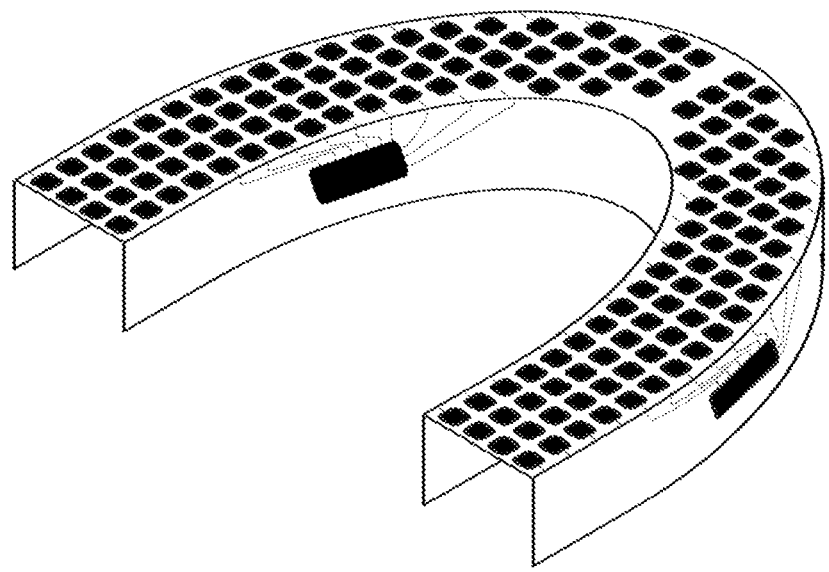
FIG. 12 depicts a device of the invention shaped as a dental fork. Array of sensors are placed in the biting region and opportunely connected with micro-controllers.

FIG. 12 shows an embodiment of the invention, namely a pressure sensitive bite fork assembly which includes a biocompatible ultra-thin substrate in which the capacitive sensors, transmission conductive lines and electronic components are embedded in three different layers. The substrate parts and the transmission conductive lines are stretchable and flexible. The shape of the bite fork is conformal with the human dental ark. The dental fork includes an array of multiple sensors placed in the biting region.

When the patient bites the device, the relative distance between the pads changes affecting the sensor electrical performances consequently. This electrical performance variation is processed by a set of micro-controllers in order to calculate the load position and the relative intensity. The force applied to each sensor is computed independently.

Figure 5:
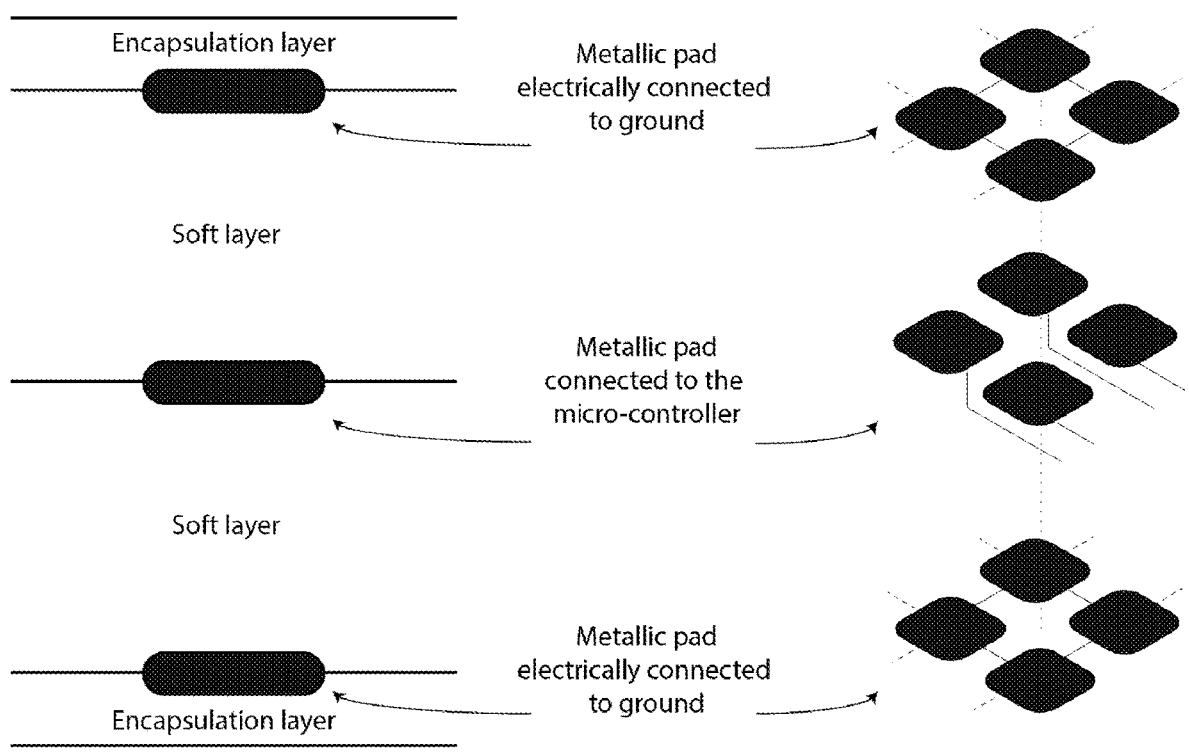
FIG. 5 depicts a view of a possible layout of the stacked metallic pads.
Figure 13:
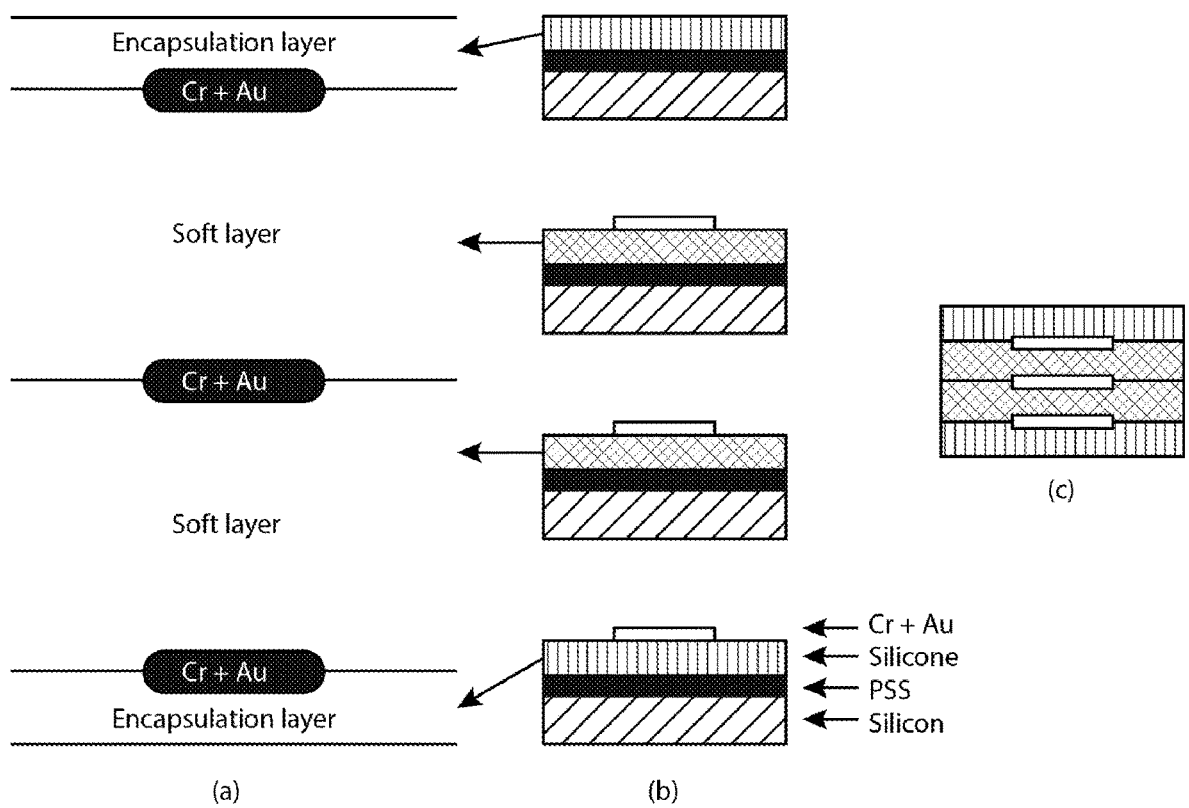
FIG. 13 depicts the sensor fabrication process. Left: the stacked layout. Middle: each layer is fabricated separately. Right: the layers are peeled off, cut and bonded.

In order to shield the capacitive sensors, the most external pads are connected to ground, shielding the internal one from external disturbs. The particularity is that the sensor remains:

Stretchable and so fully conformable to the teeth profile
Flexible
Bio-compatible and implantable The layout shown in FIG. 5 has been fabricated in multiple steps. The process flow is schematically illustrated in FIG. 13. To hold the used flexible silicone layers during the process, commercially available silicon wafers are used as substrate. Each layer is processed separately and then bonded together by oxygen plasma treatment. For each layer, a releasing poly sodium 4-styrenesulfonate (PSS) layer is spin-coated up to 10 µm thickness on a silicon wafer. PSS helps in peeling off the upper layer from the wafer once the process is performed. Then silicone (e.g. PDMS, ECOFLEX) is spin-coated for about 20 µm and cured on the planarization stage. In the depicted embodiment, PDMS has been used for the encapsulating layers (the external ones) while ECOFLEX silicone (which is softer than PDMS) for the layers between the capacitor armatures. The armatures of the capacitors and the electrical connections are realized by metal (Cr+Au) evaporation; a 5 nm layer of chrome is evaporated on silicone to improve the adhesion of the successive 30 nm gold layer. A silicon shadow mask is properly aligned on the wafer in order to realize the desired pattern. The layers are then bonded in order to create the final sensor assembly.

Depending on the applications, a rigid plate, made of plastic or metal, can be encapsulated in contact with the external gold pads to stiffen the capacitor armatures while keeping stretchable the connections to the sensor.

The invention claimed is:

1. A device for measuring dental occlusion of a subject by capacitive measurement, comprising:
   a substrate reversibly deformable upon the dental occlusion; and
   a sensor incorporated within the substrate including an array of stretchable capacitive pads that reversibly deform according to a deformation of the substrate upon the dental occlusion, each stretchable capacitive pad connected to a transmission conductive line, the transmission conductive line operatively connecting the respective stretchable capacitive pad to a micro controller.

2. The device of claim 1, wherein at least one of the stretchable capacitive pad and the transmission conductive lines are made of at least one of a conductive metallic and polymeric material.

3. The device of claim 1, wherein the substrate comprises an elastomeric material.

4. The device of claim 1, wherein the transmission conductive lines are also deformable according to the deformation of the substrate upon the dental occlusion.

5. The device of claim 1, wherein the device is shaped as a bite fork.

6. The device of claim 1, further comprising:
   at least two shield layers embedded in the substrate located respectively above and under the sensor and connected to ground,
   wherein the at least two shield layers are shaped to reduce an electromagnetic interaction between a body part of the subject and the transmission conductive lines of the sensor due to a proximity effect.

7. The device of claim 1, wherein the stretchable capacitive pad includes:
   three electrode pads and a dielectric flexible material, one of the three electrode pads operatively connected to the micro controller and embedded in the dielectric flexible material and sandwiched between the other two electrode pads, the other two electrode pads being connected to ground.

8. A device for measuring at least one of load and a force applied over all or a part of a dental arch of a subject upon at least one of clenching and dental occlusion, by capacitive measurement, comprising:
   a substrate reversibly deformable upon at least one of the clenching and the dental occlusion;
   a sensor incorporated within the substrate including an array of stretchable capacitive pads that reversibly deform according to a deformation of the substrate upon the dental occlusion, each stretchable capacitive pad connected to a transmission conductive line, the transmission conductive line operatively connecting the respective stretchable capacitive pad to a micro controller; and
   at least a two shielding pads incorporated within the substrate and located respectively above and under the sensor and in correspondence therewith,
   wherein the at least two shielding pads are connected through transmission conductive lines to ground.

9. The device of claim 8, wherein the at least two shielding pads include an array of stretchable capacitive pads.

10. The device of claim 8, wherein at least one of the stretchable capacitive pad, the shielding pads, and the transmission conductive lines are made of a conductive metallic material.

11. The device of claim 8, wherein the substrate comprises an elastomeric material.

12. The device of claim 8, wherein at least one of the transmission conductive lines and the shielding pads are also deformable according to the deformation of the substrate upon at least one of the clenching and the dental occlusion.

13. The device of claim 8, wherein the device is shaped as a bite fork.

14. The device of claim 8, further comprising:
at least two shield layers embedded in the substrate located respectively above and under at least one of the sensor and the shielding pads, and connected to ground, wherein the at least two shield layers are shaped to reduce an electromagnetic interaction between a body part of the subject and the transmission conductive lines of the sensor due to a proximity effect.

15. The device of claim 8, wherein the stretchable capacitive pad includes:
three electrode pads and a dielectric flexible material, one of the three electrode pads operatively connected to the micro controller and embedded in the dielectric flexible material and sandwiched between the other two electrode pads, the other two electrode pads being connected to ground.

16. A system for measuring at least one of a load and a force applied over all or part of a dental arch of a subject upon at least one of clenching and dental occlusion, comprising:
a device including,
a substrate reversibly deformable upon at least one of the clenching and the dental occlusion, and
a capacitive sensor incorporated within the substrate including an array of stretchable capacitive pads that reversibly deform according to a deformation of the substrate upon the dental occlusion, each stretchable capacitive pad connected to a transmission conductive line, the transmission conductive line operatively connecting the respective stretchable capacitive pad to a micro controller; and
an output system operatively connected to the micro controller of the device for analyzing and at least one of graphically and numerically displaying at least one of the load and the force applied over the dental arch upon at least one of the clenching and the dental occlusion.

17. The system of claim 16, wherein the stretchable capacitive pad includes:
three electrode pads and a dielectric flexible material, one of the three electrode pads operatively connected to the micro controller and embedded in the dielectric flexible material and sandwiched between the other two electrode pads, the other two electrode pads being connected to ground.

18. A method for measuring at least one of a load and a force applied over all or part of a dental arch of a subject upon at least one of clenching and dental occlusion, the method comprising the steps of:
at least one of clenching and occluding teeth by the subject by biting a capacitive measurement device; and
measuring at least one of the load and the force applied over the dental arch upon the biting the capacitive measurement device,
wherein the capacitive measurement device includes,
a substrate reversibly deformable upon performance of the step of at least one of the clenching and the dental occlusion, and
a capacitive sensor incorporated within the substrate including an array of stretchable capacitive pads that reversibly deform according to a deformation of the substrate upon the dental occlusion, each stretchable capacitive pad connected to a transmission conductive line, the transmission conductive line operatively connecting the respective stretchable capacitive pad to a micro controller for the step of measuring.

19. The method of claim 18, wherein the stretchable capacitive pad includes:
three electrode pads and a dielectric flexible material, one of the three electrode pads operatively connected to the micro controller and embedded in the dielectric flexible material and sandwiched between the other two electrode pads, the other two electrode pads being connected to ground.

\* \* \* \* \*